US011688300B2

(12) United States Patent
Medan et al.

(10) Patent No.: US 11,688,300 B2
(45) Date of Patent: Jun. 27, 2023

(54) DIAGNOSIS AND TREATMENT OF SPEECH AND LANGUAGE PATHOLOGIES BY SPEECH TO TEXT AND NATURAL LANGUAGE PROCESSING

(71) Applicant: Amplio Learning Technologies Ltd., Haifa (IL)

(72) Inventors: Yoav Medan, Haifa (IL); Yair Shapira, Haifa (IL); Liron Mick, Tel Aviv (IL)

(73) Assignee: AMPLIO LEARNING TECHNOLOGIES LTD., Haifa (IL)

( * ) Notice: Subject to any disclaimer, the term of this patent is extended or adjusted under 35 U.S.C. 154(b) by 0 days.

(21) Appl. No.: 17/046,775

(22) PCT Filed: Apr. 17, 2019

(86) PCT No.: PCT/IL2019/050437
§ 371 (c)(1),
(2) Date: Oct. 10, 2020

(87) PCT Pub. No.: WO2019/207573
PCT Pub. Date: Oct. 31, 2019

(65) Prior Publication Data

US 2021/0118329 A1     Apr. 22, 2021

Related U.S. Application Data

(60) Provisional application No. 62/662,532, filed on Apr. 25, 2018.

(51) Int. Cl.
*G09B 19/04* (2006.01)
*G06F 40/284* (2020.01)
(Continued)

(52) U.S. Cl.
CPC ............ *G09B 19/04* (2013.01); *A61B 5/0048* (2013.01); *A61B 5/165* (2013.01); *A61B 5/4803* (2013.01);
(Continued)

(58) Field of Classification Search
CPC ............ G09B 19/04; G09B 5/04; G09B 5/06
See application file for complete search history.

(56) References Cited

U.S. PATENT DOCUMENTS 9,072,478 B1 *   7/2015   Feerst .................... G09B 5/065
2009/0171661 A1 *   7/2009   Jayadeva ................ G10L 15/26
                                                                704/250
(Continued)

FOREIGN PATENT DOCUMENTS

WO       2017008075 A1      1/2017

OTHER PUBLICATIONS

PCT Search Report for International Application No. PCT/IL2019/050437 dated Jul. 25, 2019, 3 pp.
(Continued)

*Primary Examiner* — Peter R Egloff
(74) *Attorney, Agent, or Firm* — The Roy Gross Law Firm, LLC; Roy Gross

(57) ABSTRACT

There is provided herein a method for assessing a speech/lingual quality of a subject, the method comprising: providing a content-containing stimulus to a user; recording the user's vocal response to the stimulus and/or to instructions related thereto; processing the user's recorded vocal response to measure/extract/compute at least one linguistics (prosodic) parameter and at least one acoustic parameter; transforming the user's vocal response into a transformed text section, which is based on a processing unit's interpretation of the user's verbal response; comparing the transformed text section to a predetermined text section, which
(Continued)

represents the user's expected; and computing an output signal indicative of at least one speech/lingual quality of the user, based at least on data resulted from the texts comparison, the at least one measured/extracted/computed linguistic parameter and the at least one acoustic parameter.

14 Claims, 2 Drawing Sheets

(51) Int. Cl.
    *A61B 5/00*     (2006.01)
    *A61B 5/16*     (2006.01)
    *G09B 5/06*     (2006.01)
    *G10L 15/18*     (2013.01)
    *G10L 15/22*     (2006.01)
    *G10L 25/60*     (2013.01)

(52) U.S. Cl.
    CPC .......... *A61B 5/7264* (2013.01); *G06F 40/284* (2020.01); *G09B 5/06* (2013.01); *G10L 15/1807* (2013.01); *G10L 15/22* (2013.01); *G10L 25/60* (2013.01)

(56) References Cited

U.S. PATENT DOCUMENTS

| | | | |
|---|---|---|---|
| 2013/0304472 A1 | 11/2013 | Pakhomov | |
| 2014/0342324 A1* | 11/2014 | Ghovanloo | G09B 5/06 434/185 |
| 2014/0356822 A1* | 12/2014 | Hoque | G09B 19/04 434/185 |
| 2015/0006170 A1* | 1/2015 | Caskey | G09B 19/06 704/235 |
| 2015/0248898 A1* | 9/2015 | Loukina | G09B 19/04 704/239 |
| 2016/0049094 A1* | 2/2016 | Gupta | G09B 9/00 434/185 |

OTHER PUBLICATIONS

PCT Written Opinion for International Application No. PCT/IL2019/050437 dated Jul. 25, 2019, 4 pp.

PCT Preliminary Report on Patentability for International Application No. PCT/IL2019/050437 dated Oct. 27, 2020, 5 pp.

\* cited by examiner

DIAGNOSIS AND TREATMENT OF SPEECH AND LANGUAGE PATHOLOGIES BY SPEECH TO TEXT AND NATURAL LANGUAGE PROCESSING

CROSS REFERENCE TO RELATED APPLICATIONS

This application is a National Phase of PCT Patent Application No. PCT/IL2019/050437 having International filing date of Apr. 17, 2019, which claims the benefit of priority of U.S. Provisional Application No. 62/662,532 filed on Apr. 25, 2018 entitled DIAGNOSIS AND TREATMENT OF SPEECH AND LANGUAGE PATHOLOGIES BY SPEECH TO TEXT AND NATURAL LANGUAGE PROCESSING. The contents of the above applications are all incorporated by reference as if fully set forth herein in their entirety.

FIELD OF THE INVENTION

Embodiments of the disclosure relate to speech/language pathologies.

BACKGROUND

Speech is generated by a coordinated motion of the vocal chords and the various articulatory organs (such as lips, tongue and jaw). Like any vocal instrument, one needs to practice in order to coordinate it correctly. Language skills depend on the phonological, semantical, grammatical, lexical and planning abilities of the individual.

People with speech and/or language pathologies often seek help of a speech and language pathologist (SLP) in order to acquire techniques for alleviating or at least minimizing it. Such training normally happens in a one-on-one clinical setting and without any control of the SLP over the frequency, duration, content and quality of any practice sessions of the patient, outside of the clinic.

There is a need in the art for improved and efficient methods and systems for diagnosing and treating speech/language related pathologies.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to some embodiments, there are provided herein methods and systems for providing a fully instrumented practice experience with objective scoring using Speech Quality (SQ)/language metrics and analytics. Some of the information is generated in real-time for providing a live biofeedback to the user. Some of the information may be computed at the end of the practice session and available to the user and/or to the SLP.

According to some embodiments, there is provided herein method for assessing a speech/lingual quality of a subject, the method comprising: providing a content-containing stimulus to a user; recording the user's vocal response to the stimulus and/or to instructions related thereto; processing the user's recorded vocal response to measure/extract/compute at least one linguistics (prosodic) parameter and at least one acoustic parameter; transforming the user's vocal response into a transformed text section, which is based on a processing unit's interpretation of the user's verbal response; comparing the transformed text section to a predetermined text section, which represents the user's expected response; and computing an output signal indicative of at least one speech/lingual quality of the user, based at least on data resulted from the texts comparison, the at least one measured/extracted/computed linguistic parameter and acoustic parameter.

According to some embodiments, there is provided herein a computer implemented method for assessing a speech/lingual quality of a subject, the method comprising: providing a content-containing stimulus to a user; recording the user's vocal response to the stimulus and/or to instructions related thereto; processing the user's recorded vocal response to measure/extract/compute at least one linguistics (prosodic) parameter and at least one acoustic parameter; transforming the user's vocal response into a transformed text section, which is based on a processing unit's interpretation of the user's verbal response; comparing the transformed text section to a predetermined text section, which represents the user's expected response; and computing an output signal indicative of at least one speech/lingual quality of the user, based at least on data resulted from the texts comparison, the at least one measured/extracted/computed linguistic parameter and acoustic parameter.

According to some embodiments, there is further provided herein a processing unit for assessing a speech/lingual quality of a subject, the processing unit comprising: a vocal input module configured to receive a recorded vocal sample created by a user's response to content-containing stimulus and/or to instructions related thereto; a speech processing module configured to measure/compute at least one linguistic parameter and at least one acoustic parameter relating to the user's vocal response; a vocal-to-text module configured to transform the user's verbal response into a transformed text section; a comparison module configured to compare between the transformed text section and a predetermined text section, which represents the user's expected response; and an output module configured to compute an output signal indicative of at least one speech/lingual quality of the user, based at least on data resulted from the texts comparison, the at least one measured/extracted/computed linguistic parameter and the at least one acoustic parameter.

According to some embodiments, there is further provided herein a system for assessing a speech/lingual quality of a subject, the system comprising: a prompter configured to provide a content-containing stimulus to a user; a recorder configured to record a vocal sample created by the user's response to content-containing stimulus and/or to instructions related thereto; and a processing unit comprising: a vocal input module configured to receive a recorded vocal sample created by a user's response to content-containing stimulus and/or to instructions related thereto; a speech processing module configured to measure/compute at least one linguistic parameter and at least one acoustic parameter relating to the user's vocal response; a vocal-to-text module configured to transform the user's verbal response into a transformed text section; a comparison module configured to compare between the transformed text section and a predetermined text section, which represents the user's expected response; and an output module configured to compute an output signal indicative of at least one speech/lingual quality of the user, based at least on data resulted from the texts comparison, the at least one measured/extracted/computed linguistic parameter and the at least one acoustic parameter.

According to some embodiments, computing the output signal may include assigning a speech quality score representing deviation from a norm. According to some embodiments, computing the output signal may include assigning a lingual quality score representing deviation from a norm.

According to some embodiments, the at least one speech quality may include a sub-set of speech qualities.

According to some embodiments, computing the output signal may include computing a multi parametric vector.

According to some embodiments, the stimulus provided to the user may include a text, image, video, voice stimulus, or any combination thereof.

According to some embodiments, computing the level of similarity between the transformed text section and the predetermined text section is determined based on text content parameters.

According to some embodiments, the at least one acoustic parameter may include a temporal parameter.

According to some embodiments, the at least one temporal parameter may include the user's response time, speech rate, length of prolongation, length of blocking, lengthy of pauses between words, or any combination thereof.

According to some embodiments, the at least one acoustic parameter relates to redundancies, interjections, speech intonation, tone, stress, rhythm, intensity, pitch, loudness, mental state or any combination thereof.

According to some embodiments, the at least one linguistic parameter relates to vocabulary, phonology, morphology, syntax, semantics, lexical status, pragmatics or any combination thereof.

According to some embodiments, computing an output signal indicative of the user's speech quality, may include applying natural language processing (NLP) algorithms.

According to some embodiments, the natural language processing (NLP) algorithms may include machine learning algorithms.

According to some embodiments, the machine learning algorithms may include decision trees, neural networks, statistical models, or a combination thereof.

According to some embodiments, the statistical models may include assigning a weight value to each of the parameters or sets of parameters.

According to some embodiments, parameters related to the multi parametric vector may include phonetic transcription, part of speech, semantic class, intensity, pitch, loudness, intonation, tone, stress, rhythm number of correct words, percentage of time associated with correct words, degree of acoustic similarity, degree of semantic similarity, or any combination thereof. According to some embodiments, parameters related to the multi parametric vector comprise lingual and acoustic parameters.

According to some embodiments, the lingual parameters relate to comprehension, pronunciation, planning and/or organization of correct grammar, pragmatic skills of communication, or any combination thereof.

According to some embodiments, the speech quality may include speech intelligibility. According to some embodiments, speech intelligibility comprises a degree of similarity, degree of correctness or both.

According to some embodiments, degree of similarity may include degree of acoustic similarity, degree of semantic similarity or both. According to some embodiments, degree of correctness comprises number of correct words, percentage of time associated with correct words, grammatical/phonological/semantic correctness, mistake type(s) or any combination thereof.

According to some embodiments, the method may further include providing a feedback signal to the user and/or to a care giver. Such feedback may indicate, for example, a progress of a user, a need to change treatment/practice protocol, a score or any other relevant information.

According to some embodiments, the method may be used for treating/diagnosing a speech/lingual related pathology of a subject suffering from said pathology.

According to some embodiments, the pathology is related to a disease/condition selected from a group consisting of aphasia, ALS, Parkinson and Alzheimer's. According to some embodiments, the pathology relates to stuttering.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

Figure 1:
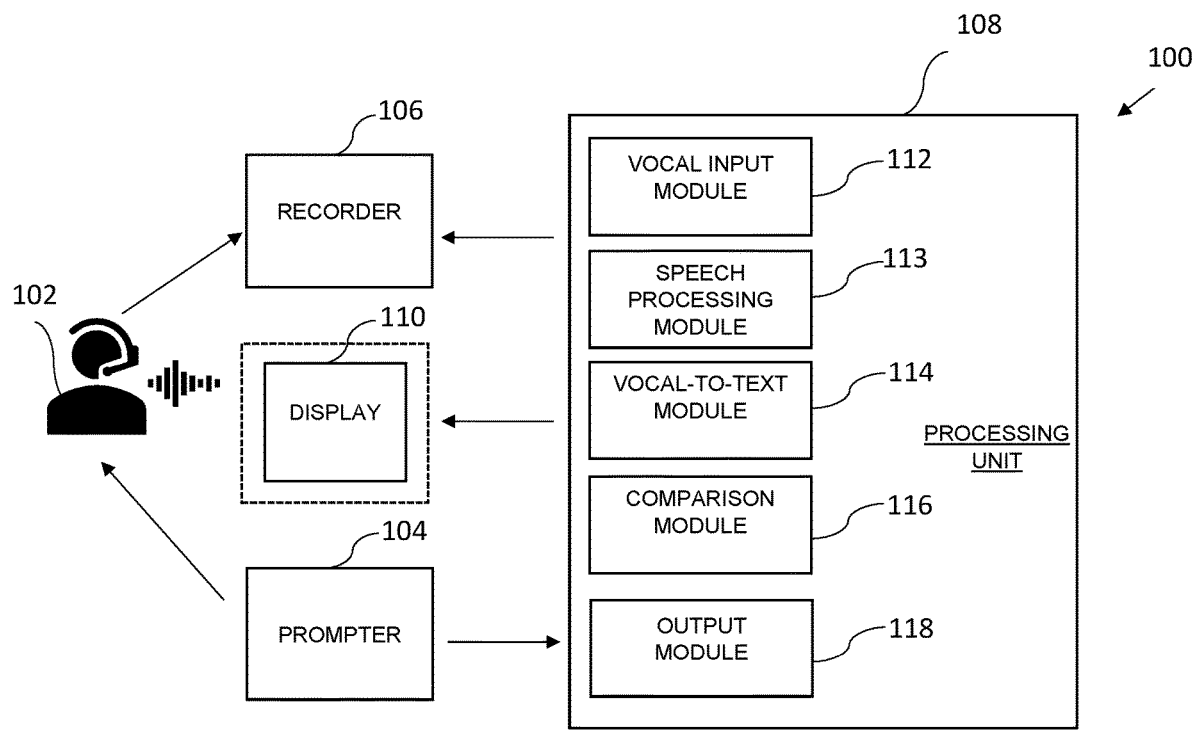
FIG. 1 schematically depicts a block diagram of a system for treating/diagnosing a speech/language related pathology, according to some embodiments.

Reference is now made FIG. 1, which schematically depicts a block diagram of a system 100 for treating/diagnosing a speech/language related pathology, according to some embodiments. System 100 is designed to diagnose and/or treat speech and/or language related pathologies in a user, such as user 102. System 100 includes a prompter 104, a recorder 106, a processing unit 108 and, optionally, a display unit 110. Processing unit 108 includes a few sub units, namely, a vocal input module 112, a speech processing module 113, vocal-to-text module 114, comparison module 116 and output module 118. System 100 may operate as follows: user 102 receives from prompter 104 a content-containing stimulus and, optionally, also a set of instructions or questions corresponding to the stimulus. The content-containing stimulus may include, for example, a text section, a picture, an image, a video clip, a vocal section or any other meaningful stimulus. User 102 is then requested to provide a vocal (verbal) response to the stimulus. The user may be requested to respond by reading the text represented to him/her, describing the presented picture/image, following instructions related to the stimulus and/or answering some questions or by any other vocal verbal way. The user's vocal (verbal) response to the stimulus is recorded by recorder 106 and the recording signals are transferred to processing unit 108 for further processing and analysis. The recorded input is received by vocal input module 112 and processed by a speech processing module 113 to measure/extract/compute prosodic (linguistic) parameters relating to the user's vocal response. The recorded input is further transformed, by vocal-to-text module 114, into a text section (which may also be referred to as a "transformed text section"). The vocal-to-text transformation is based on the system's interpretation of the user's vocal (verbal) response to the stimulus. Comparison module 116 is configured to receive the transformed text section, to compare it to a predetermined text section, which represents the user's expected response to the same stimulus. Output module 118 is configured to compute, a multi parametric vector, based at least on data resulted from the texts comparison and on the measured/extracted/compute prosodic (linguistic) parameters and to provide an output signal indicative of the user's speech quality (qualities). In other words, the user's speech quality is at least partially determined by the level of similarity between his/her response to the stimulus and the expected response and on linguistic characteristics. For example, if the user stutters, omit words, mispronounces words/syllables, has a long response time, speaks very slowly/fast, "swallows" words, etc., the linguistic parameters (such as speech rhythm) will be assessed as poor and the level of similarity between his/her response to the stimulus and the expected response will be low. In this case, the speech quality will be defined as "low". If, on the other hand, the user's pronunciation, articulation and other speech/lingual related parameters are good, the linguistic parameters will be assessed as good and the level of similarity between his/her response to the stimulus and the expected response will be high, and the speech quality will be defined as "high". It is noted that the system and methods disclose herein may, in accordance with some embodiments, compute one or more speech qualities. For example, a subject may be diagnosed with high fluency (which is one type of speech quality) but with medium or low reaction time (which is a different type of speech quality). Each determined speech quality may be assigned a score, for example 1-10 or 1-100, and may be displayed on display unit 110 for the user's consideration or for the consideration or follow-up of a caregiver such as a speech and language pathologist (SLP). Display unit 110 may also present a trend of improvement/deterioration, recommendations, suggestions for practice, etc.

Figure 2:
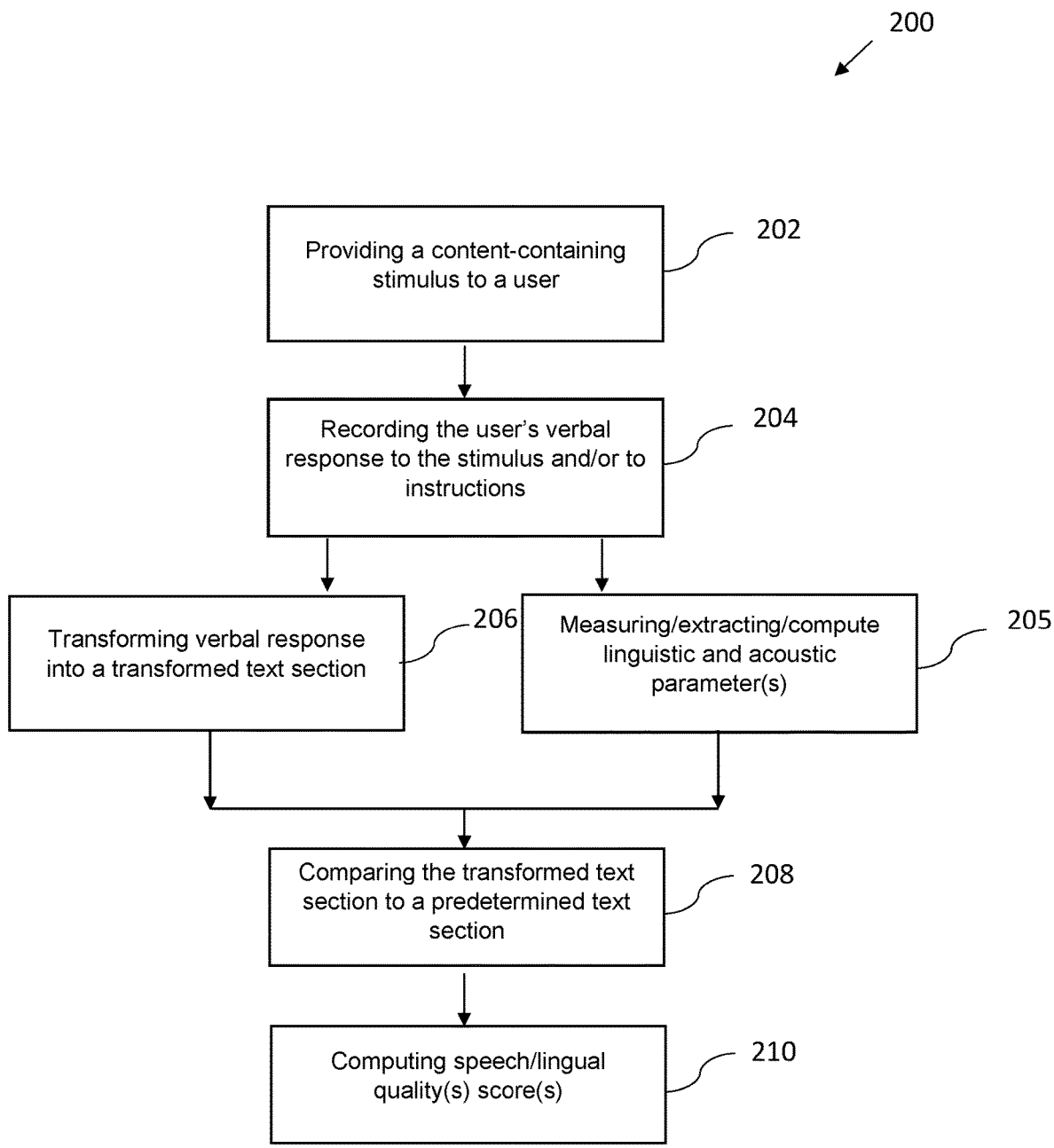
FIG. 2 schematically depicts a flowchart of a method for treating/diagnosing a speech/language related pathology, according to some embodiments.

Reference is now made FIG. 2, which schematically depicts a flowchart 200 of a method for treating/diagnosing a speech/language related pathology, according to some embodiments. The method includes the following steps:

Step 202—providing a content-containing stimulus to a user. As disclosed herein, such stimulus may include a text section, a picture, an image, a video clip, a vocal section or any other meaningful stimulus to which the user is requested to respond by reading the text, describing the picture/image, following instructions or answering questions related to the presented stimulus.

Step 204—recording the user's vocal (which is also verbal) response to the stimulus and/or to instructions related to thereto.

Step 205—processing the user's recorded vocal response to measure/extract compute at least one prosodic (linguistics) parameter;

Step 206—transforming the user's verbal response into a transformed text section, which is based on the system's interpretation of the user's verbal response. For example, in case A, the user clearly pronounces a certain word, the system will transform it into the same textual word. In case B, on the other hand, the user mispronounces the word, the system may misinterpret the word and transform it into a different textual word.

Step 208—comparing the transformed text section to a predetermined text section, which represents the user's expected response and providing data representing a level of similarity between the transformed text section and a predetermined text section.

Step 210—computing a multi parametric vector, based at least on data resulted from the texts comparison and the measured/extracted/compute prosodic parameters, and providing an output signal indicative of one or more of the user's speech/lingual/qualities.

For example, in case A described above, where the user clearly pronounced the certain word and the system transformed this vocally pronounced word into the same textual word, the level of similarity between the transformed text section and a predetermined text section is high and the speech quality is determined to be good. On the other hand, in case B described above, where the user mispronounced the word and the system thus misinterpreted the vocally pronounced word and transformed it into a different textual word, the level of similarity between the transformed text section and the predetermined text section is low and the speech quality is determined to be poor.

It is noted that the examples provided are simplified and non-limiting and are presented herein merely for explanatory purpose.

The method may further include providing feedback to the user or to the SLP regarding the results of each recording session and may also provide speech quality trends or a trend of selected speech/language parameter(s).

There are provided herein, according to some embodiments, examples of speech/language pathologies that may be detected, diagnosed, monitored and/or treated by the methods and systems provided herein:

Stuttering—e.g., prolongations, repetitions, blocking etc.

Pronunciation pathologies—the system may detect the level of similarity between actual pronunciation and desired pronunciation.

Phonation (producing sound)—the system may detect the level of similarity between actual phonation and desired phonation.

Voice—the system may detect the level of similarity between actual vocal parameters (such as pitch, intonation and intensity) and desired vocal parameters.

Fluency—the system may detect the level of similarity between actual and desired fluency.

Language—the system may detect the level of similarity between actual and desired lingual parameters (such as vocabulary, phonology, morphology, syntax, semantics, lexical status, and pragmatics).

According to some embodiments, the system and methods disclosed herein may be used for detecting, follow-up and/or treating speech/language related pathologies of Parkinson patients.

According to some embodiments, the system and methods disclosed herein may be used for detecting, follow-up and/or treating subjects suffering from speech/lingual related pathologies such as speech/language behavioral, developmental, rehabilitation and/or degenerative conditions/diseases. Example of conditions/diseases may include aphasia, Parkinson, Alzheimer's, ALS, stuttering etc.

In the description and claims of the application, each of the words "comprise" "include" and "have", and forms thereof, are not necessarily limited to members in a list with which the words may be associated.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What we claim is:

1. A computerized method for assessing a speech and/or lingual quality of a subject, and treating and/or diagnosing a speech and/or lingual related pathology, the method comprising:
   providing a content-containing stimulus to a user;
   recording the user's vocal response to the stimulus and/or to instructions related thereto;
   extracting and/or measuring and/or computing at least one prosodic parameter and at least one acoustic parameter from the user's recorded vocal response by a processing unit, wherein the at least one acoustic parameter comprises a temporal parameter which comprises the user's response time;
   identifying the words in the user's vocal response by the processing unit and transforming the user's vocal response into a transformed text section, based on the identified words in the user's vocal response;
   comparing the transformed text section to a predetermined text section via the processing unit, which represents the user's expected response;
   computing by the processing unit, an output signal indicative of at least one speech and/or lingual quality of the user, which comprises computing a multi parametric vector, based at least on data resulted from the texts comparison, the at least one extracted and/or measured and/or computed prosodic parameter and acoustic parameter; and
   detecting a speech and/or lingual related pathology of the subject suffering from said pathology based upon the output signal, wherein the speech and/or lingual related pathology is selected from a group consisting of aphasia, ALS, Parkinson, Alzheimer's and stuttering;
   wherein computing an output signal indicative of the user's speech quality, comprises applying natural language processing (NLP) algorithms,
   wherein the natural language processing (NLP) algorithms comprise machine learning algorithms,
   wherein the machine learning algorithms comprise decision trees, neural networks, statistical models, or a combination thereof, and
   wherein the statistical models comprise assigning a weight value to each of the parameters or sets of parameters and wherein the weight value is displayed on a display.

2. The method of claim 1, wherein computing the output signal comprises assigning a speech quality score representing deviation from a norm.

3. The method of claim 1, wherein computing the output signal comprises assigning a lingual quality score representing deviation from a norm.

4. The method of claim 1, wherein the at least one speech quality comprises a sub-set of speech qualities.

5. The method of claim 1, wherein the stimulus provided to the user comprises a text, image, video, voice stimulus, or any combination thereof.

6. The method of claim 1, wherein computing the level of similarity between the transformed text section and the predetermined text section is determined based on text content parameters.

7. The method of claim 1, wherein the at least one temporal parameter further comprises the user's speech rate, length of prolongation, length of blocking, lengthy of pauses between words, or any combination thereof.

8. The method of claim 1, wherein the at least one acoustic parameter relates to redundancies, interjections, speech intonation, tone, stress, rhythm, intensity, pitch, loudness, mental state or any combination thereof.

9. The method of claim 1, wherein the at least one linguistic parameter relates to vocabulary, phonology, morphology, syntax, semantics, lexical status, pragmatics or any combination thereof.

10. The method of claim 1, wherein parameters related to the multi parametric vector comprise phonetic transcription, part of speech, semantic class, intensity, pitch, loudness, intonation, tone, stress, rhythm number of correct words, percentage of time associated with correct words, degree of acoustic similarity, degree of semantic similarity, or any combination thereof.

11. The method of claim 1, wherein parameters related to the multi parametric vector comprise lingual and acoustic parameters.

12. The method of claim 11, wherein the lingual parameters relate to comprehension, pronunciation, planning and/or organization of correct grammar, pragmatic skills of communication, or any combination thereof.

13. A processing unit for assessing a speech and/or lingual quality of a subject, and treating and/or diagnosing a speech and/or lingual related pathology, the processing unit comprising:
   a vocal input sub-unit executing a code configured to receive a recorded vocal sample created by a user's response to content-containing stimulus and/or to instructions related thereto;
   a speech processing sub-unit executing a code configured to extract and/or measure and/or compute at least one prosodic parameter and at least one acoustic parameter relating to the user's vocal response, wherein the at least one acoustic parameter comprises a temporal parameter which comprises the user's response time;
   a vocal-to-text sub-unit executing a code configured to transform the user's verbal response into a transformed text section;

a comparison sub-unit executing a code configured to compare between the transformed text section and a predetermined text section, which represents the user's expected response; and an output unit executing a code configured to:
compute an output signal indicative of at least one speech and/or lingual quality of the user, which comprises computing a multi parametric vector, based at least on data resulted from the texts comparison, the at least one extracted and/or measured and/or computed prosodic parameter and the at least one acoustic parameter; and detect a speech and/or lingual related pathology of the subject suffering from said pathology based upon the output signal wherein the speech and/or lingual related pathology is selected from a group consisting of aphasia, ALS, Parkinson, Alzheimer's and stuttering;

wherein computing an output signal indicative of the user's speech quality, comprises applying natural language processing (NLP) algorithms, wherein the natural language processing (NLP) algorithms comprise machine learning algorithms, wherein the machine learning algorithms comprise decision trees, neural networks, statistical models, or a combination thereof, and wherein the statistical models comprise assigning a weight value to each of the parameters or sets of parameters and wherein the weight value is displayed on a display.

14. A system for assessing a speech and/or lingual quality of a subject, and treating and/or diagnosing a speech and/or lingual related pathology, the system comprising:

a prompter configured to provide a content-containing stimulus to a user;

a recorder configured to record a vocal sample created by the user's response to content-containing stimulus and/or to instructions related thereto; and a processing unit comprising:
a vocal input sub-unit executing a code configured to receive a recorded vocal sample created by a user's response to content-containing stimulus and/or to instructions related thereto;

a speech processing sub-unit executing a code configured to extract and/or measure and/or compute at least one prosodic parameter and at least one acoustic parameter relating to the user's vocal response, wherein the at least one acoustic parameter comprises a temporal parameter which comprises the user's response time;

a vocal-to-text sub-unit executing a code configured to transform the user's verbal response into a transformed text section;

a comparison sub-unit executing a code configured to compare between the transformed text section and a predetermined text section, which represents the user's expected response; and an output sub-unit executing a code configured to:
compute an output signal indicative of at least one speech and/or lingual quality of the user, which comprises computing a multi parametric vector, based at least on data resulted from the texts comparison, the at least one extracted and/or measured and/or computed prosodic parameter and the at least one acoustic parameter; and detect a speech and/or lingual related pathology of the subject suffering from said pathology based upon the output signal wherein the speech and/or lingual related pathology is selected from a group consisting of aphasia, ALS, Parkinson, Alzheimer's and stuttering;

wherein computing an output signal indicative of the user's speech quality, comprises applying natural language processing (NLP) algorithms, wherein the natural language processing (NLP) algorithms comprise machine learning algorithms, wherein the machine learning algorithms comprise decision trees, neural networks, statistical models, or a combination thereof, and wherein the statistical models comprise assigning a weight value to each of the parameters or sets of parameters and wherein the weight value is displayed on a display.

\* \* \* \* \*